United States Patent
Manzanares (10) Patent No.: US 8,808,172 B2
(45) Date of Patent: Aug. 19, 2014

(54) METHOD AND APPARATUS FOR LATERALLY ACCESSING AN INTERVERTEBRAL DISC SPACE

(75) Inventor: James Manzanares, Bonita Springs, FL (US)

(73) Assignee: DePuy Synthes Products, LLC, Raynham, MA (US)

( * ) Notice: Subject to any disclaimer, the term of this patent is extended or adjusted under 35 U.S.C. 154(b) by 146 days.

(21) Appl. No.: 12/991,018

(22) PCT Filed: May 7, 2009

(86) PCT No.: PCT/US2009/043177
§ 371 (c)(1),
(2), (4) Date: Nov. 4, 2010

(87) PCT Pub. No.: WO2009/137700
PCT Pub. Date: Nov. 12, 2009

(65) Prior Publication Data
US 2011/0065999 A1    Mar. 17, 2011

Related U.S. Application Data (60) Provisional application No. 61/051,271, filed on May 7, 2008.

(51) Int. Cl.
  *A61B 1/32*   (2006.01)
  *A61B 17/02*  (2006.01)
  *A61B 19/00*  (2006.01)
  *A61B 17/00*  (2006.01)

(52) U.S. Cl.
  CPC ............ *A61B 17/0218* (2013.01); *A61B 19/26* (2013.01); *A61B 2017/00261* (2013.01)
  USPC .......... 600/201; 600/210; 600/215; 600/224; 600/227; 606/86 A (58) Field of Classification Search
  USPC ................ 600/201, 204, 206, 208, 210, 211, 600/213–216, 219, 221, 222, 224, 236, 600/227–234; 606/86 A, 90, 99, 108, 279; 604/164.1, 164.11, 164.01, 910, 604/164.04, 174, 178, 164.02, 167.03, 604/167.05
  See application file for complete search history.

(56) References Cited

U.S. PATENT DOCUMENTS 3,782,370 A * 1/1974 McDonald .................... 600/207
3,789,852 A * 2/1974 Kim et al. ..................... 604/104

(Continued)

FOREIGN PATENT DOCUMENTS

EP            1454589        4/2006
WO    WO 2006/086663        8/2006

(Continued)

*Primary Examiner* — Michael T Schaper
*Assistant Examiner* — Tracy Kamikawa
(74) *Attorney, Agent, or Firm* — Baker & Hostetler LLP (57) ABSTRACT

A method for laterally accessing a lumbosacral intervertebral disc space of a patient includes positioning the patient laterally and making an incision to provide lateral access to the patient's iliac crest. A bracket (24) may be placed on the iliac crest and a retractor (28) may be attached to the bracket such that a distal end of the retractor is positioned over the lumbosacral intervertebral disc space while a proximal end of the retractor provides an entry space for a surgeon to insert at least one tool (90). The surgeon may perform a surgical procedure on the lumbosacral intervertebral disc space through a channel (49) defined by the retractor.

31 Claims, 10 Drawing Sheets

(56) References Cited

U.S. PATENT DOCUMENTS

| | | | |
|---|---|---|---|
| 4,457,300 A * | 7/1984 | Budde | 600/228 |
| 6,007,552 A * | 12/1999 | Fogarty et al. | 606/157 |
| 6,206,826 B1 | 3/2001 | Mathews et al. | |
| 6,322,500 B1 * | 11/2001 | Sikora et al. | 600/219 |
| 6,464,634 B1 * | 10/2002 | Fraser | 600/233 |
| 6,613,038 B2 * | 9/2003 | Bonutti et al. | 604/509 |
| 7,087,058 B2 | 8/2006 | Cragg | |
| 7,150,714 B2 * | 12/2006 | Myles | 600/205 |
| 7,179,225 B2 | 2/2007 | Shluzas et al. | |
| 7,290,347 B2 | 11/2007 | Augostino et al. | |
| 2002/0026101 A1 * | 2/2002 | Bookwalter et al. | 600/231 |
| 2003/0181982 A1 | 9/2003 | Kuslich | |
| 2005/0149035 A1 | 7/2005 | Pimenta et al. | |
| 2005/0159650 A1 * | 7/2005 | Raymond et al. | 600/201 |
| 2005/0234304 A1 * | 10/2005 | Dewey et al. | 600/210 |
| 2006/0106416 A1 | 5/2006 | Raymond et al. | |
| 2006/0217754 A1 | 9/2006 | Boehm, Jr. et al. | |
| 2006/0217806 A1 * | 9/2006 | Peterman et al. | 623/17.11 |
| 2006/0271096 A1 | 11/2006 | Hamada | |
| 2007/0055111 A1 | 3/2007 | Morgan et al. | |
| 2007/0100212 A1 | 5/2007 | Pimenta et al. | |
| 2007/0161867 A1 * | 7/2007 | Fowler et al. | 600/233 |
| 2007/0208227 A1 | 9/2007 | Smith et al. | |
| 2007/0233129 A1 * | 10/2007 | Bertagnoli et al. | 606/79 |

FOREIGN PATENT DOCUMENTS

| | | |
|---|---|---|
| WO | WO 2006/096532 | 9/2006 |
| WO | WO 2007085909 A2 * | 8/2007 |

* cited by examiner

METHOD AND APPARATUS FOR LATERALLY ACCESSING AN INTERVERTEBRAL DISC SPACE

CROSS-REFERENCE TO RELATED APPLICATIONS

This application is the National Stage of International Application No. PCT/US2009/043177, filed May 7, 2009, which claims the benefit of U.S. provisional Application No. 61/051,271, filed May 7, 2008, the disclosures of which are incorporated herein by reference in their entireties for all purposes.

TECHNICAL FIELD

This technology relates to systems and methods for performing minimally invasive spinal surgical procedures, and preferably to a procedure and suite of instruments for enabling lateral access to the lower lumbar area of the spine, particularly the L5-S1 intervertebral disc space.

BACKGROUND OF THE INVENTION

An estimated ten (10) million adults suffer from chronic back pain, a condition that can limit their activities. Many adults with back pain undergo traditional spine surgery, which can require months of recovery.

For quite some time, lumbar spinal fusions have been performed for a variety of spinal conditions, such as posterior, posterolateral and anterior lumbar interbody fusions, to alleviate back pain.

Lumbar spinal fusion is a common technique to help patients with back pain, who have generally been unable to alleviate their back pain with non-operative treatment. Once a patient and their physician have decided to fuse at least two vertebrae in the lumbar spine, one of a variety of procedures may be selected. The choice of technique may be dependent on the patient's specific condition or it may be predicated upon surgeon preference regarding a surgical approach to the spine, for example, the front of the spine (anterior), the back of the spine (posterior) or less invasive approaches, called Minimally Invasive Spinal (MIS) surgery. The goals of all these techniques remain the same, to achieve a lumbar fusion, and lessen the patient's pain.

The most common method of spinal fusion involves the posterior approach, with an incision along the back of the patient's spine. Often, this procedure is used if bone spurs, thickened ligaments, or disc ruptures are removed to alleviate pressure on the nerves. The fusion procedure then typically involves placement of metal screws, rods and bone graft.

Anterior spinal fusions require an incision through the abdomen. After removal of the degenerated disc, an intervertebral implant such as a metal cage, spacer, or the like alone or in combination with a bone graft is usually placed in an intervertebral disc space between vertebral bodies.

Posterior approaches may include posterior and transforaminal lumbar interbody fusions, whereas anterior techniques may include retroperitoneal and transperitoneal anterior lumbar interbody fusion approaches. At times, patients may undergo both anterior and posterior procedures.

In order to achieve adequate exposure to perform posterior and anterior procedures, an open surgical approach is traditionally performed.

As an alternative to an open surgical approach, MIS surgery techniques for lumbar fusions have been developed. MIS procedures typically have smaller incisions, may limit trauma to the surrounding tissues and may result in a faster recovery for the patient. One of these MIS techniques is a procedure that may be referred to as an extreme-lateral lumbar interbody fusion (XLIF). During the XLIF procedure the lumbar spine is typically approached from the side through a small skin incision. The surgery is performed through a muscle that lies next to the lumbar spine known as the psoas muscle, thereby avoiding the disruption of muscles and tissue in the anterior or posterior of the spine that the surgeon traditionally has had to go through to access the spine.

With the XLIF procedure, the incisions are typically smaller than those in traditional back surgeries, which generally results in minimal tissue disruption and shorter hospital stays and recovery time. For example, a patient may spend one night in the hospital compared to the five nights is some traditional surgery patients.

XLIF procedures may also be performed in combination with nerve avoidance technology. When performing the XLIF surgery with nerve avoidance technology, surgeons may be able to gain access to the spine with direct visualization, avoid nerves and stabilize the spine, while generally using traditional techniques. The technology allows surgeons to perform procedures through a minimally invasive approach. Additionally, the doctors can perform surgical procedures using instruments that are similar to those used in open procedures, but through potentially smaller incisions, while still allowing for maximum surgical access to the spine for addressing the pathology and inserting an intervertebral implant.

However, the XLIF procedure is generally contraindicated for the L5-S1 intervertebral disc space given the lumbar and sacral transitional anatomy. Discectomies associated with the L5-S1 space generally involve the mounting of various surgical instruments, such as a mounting bracket, onto support structure external to the patient, such as the guiderail of a patient support structure, a bed, a table, a gurney, or the like. Additional surgical apparatus, such as a retractor and the like, are supported by the mounting bracket for lateral access into the L5-S1 intervertebral disc space. Movement of the patient relative to the guiderail or external support structure can impact the alignment of the surgical instruments relative to the target intervertebral disc space.

It is desirable to develop a method and apparatus for accessing an intervertebral disc space, such as the L5-S1 intervertebral disc space, from a lateral approach angle wherein movement of the patient has little or no impact on the orientation of the instruments relative to the patient.

BRIEF SUMMARY OF THE INVENTION

In accordance with one embodiment, a method is provided for laterally accessing a lumbosacral intervertebral disc space. The method includes the step of making an incision in a patient to provide access to an iliac crest of the patient, mounting a bracket onto the iliac crest, attaching a retractor to the bracket such that a distal end of the retractor is positioned over the lumbosacral intervertebral disc space while a proximal end of the retractor defines a channel sized to receive at least one surgical tool, and performing a surgical procedure on the lumbosacral intervertebral disc space.

In accordance with another embodiment, a surgical kit is provided for providing lateral access to a lumbosacral intervertebral disc space.

BRIEF DESCRIPTION OF THE SEVERAL VIEWS OF THE DRAWINGS

The foregoing summary, as well as the following detailed description of a preferred embodiment of the application, will be better understood when read in conjunction with the appended drawings. For the purposes of illustrating the preferred method and apparatus for laterally accessing an intervertebral disc space of the present application, there is shown in the drawings a preferred embodiment. It should be understood, however, that the application is not limited to the precise arrangements and instrumentalities shown. In the drawings.

DETAILED DESCRIPTION OF THE INVENTION

Certain terminology is used in the following description for convenience only and is not limiting. The words "lower" and "upper" and derivatives thereof and words of similar import designate directions in the drawings to which reference is made. The words "inward" or "distal" and "outward" or "proximal" and derivatives thereof and words of similar import refer to directions toward and away from, respectively, the geometric center of the described apparatus related components thereof. The words, "anterior", "posterior", "superior," "inferior," "medial," "lateral," and derivatives thereof and words of similar import are used to designate preferred positions and orientations in the human body to which reference is made and are not meant to be limiting unless otherwise indicated.

Figure 1:
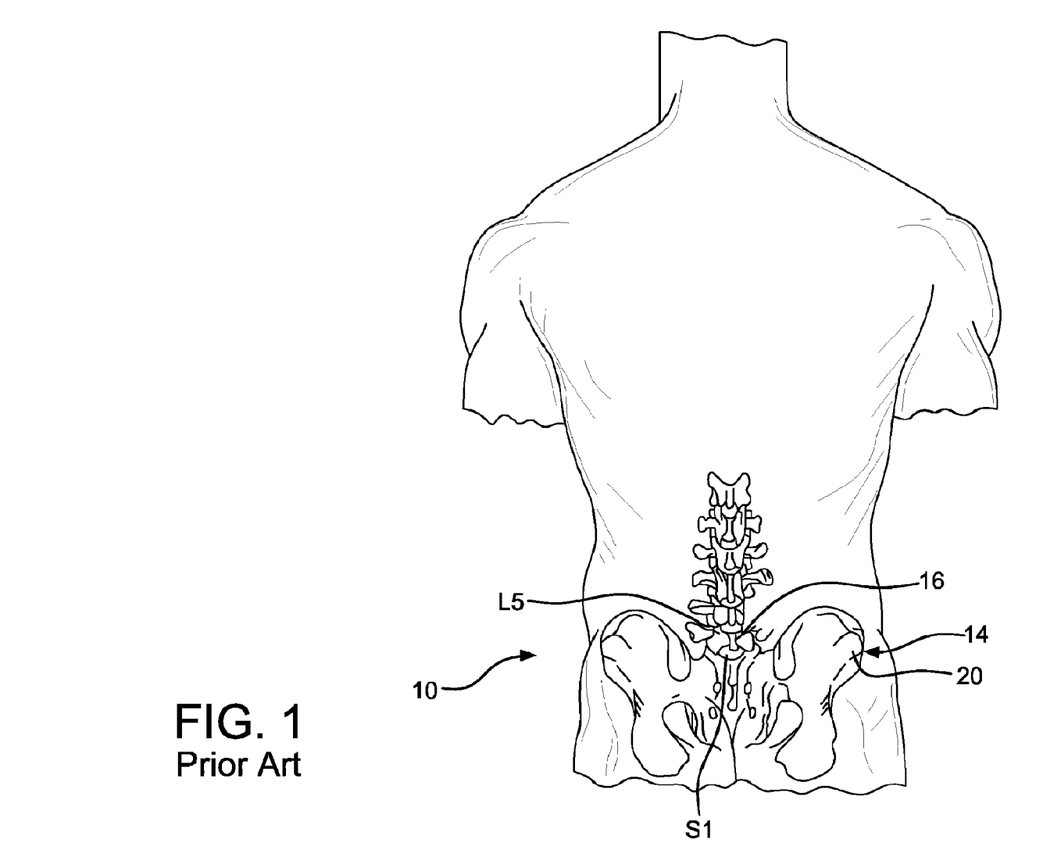
FIG. 1 is a cut-away posterior view of a lumbosacral region of a human torso.

Referring to FIG. 1, a lumbosacral region 10 of a human spine includes a lumbar vertebra, such as a fifth lumbar vertebra L5, and further includes a sacral vertebra, such as a first sacral vertebra S1. Four lumbar vertebrae are disposed above the fifth lumbar vertebra L5, such as the third and fourth lumbar vertebrae L3, L4. Embodiments described herein allow access to a planned surgical site, for instance at a lumbosacral (or L5-S1) intervertebral disc space 16. A surgical procedure can thus be performed at the intervertebral disc space 16 via a direct lateral approach to the disc space 16 along the path indicated by a direct approach arrow 14. As illustrated, an iliac crest 20 is disposed in the path of the direct approach arrow 14 and, thus, interferes with the direct lateral approach to the lumbosacral intervertebral disc space 16.

It should further be appreciated that a lumbosacral corpectomy or hemicorpectomy can be performed on disc spaces other than the lumbosacral intervertebral disc space 16, and a surgical procedure can instead be performed at an intervertebral disc space defined, for instance, between the fourth lumbar vertebra to the first sacral vertebra L4-S1 or still other vertebral bodies. Thus, the term "lumbosacral intervertebral disc space" is not intended to be limited exclusively to the disc space between the fifth lumbar vertebra L5 and the first sacral vertebra S1, unless otherwise specified.

Referring to FIGS. 2 and 5-6B, a surgical assembly or surgical kit 25 can include a mounting clamp or bracket, such as a pelvic bracket 24, a retractor 28, one or more surgical tools 90, and one or more implants 108. The pelvic bracket 24 is shown having a proximal end that is mounted onto the iliac crest 20 to provide a fixation point for the surgical instruments to be used during the surgical discectomy procedure at the lumbosacral intervertebral disc space 16. It should thus be appreciated that movement of the patient relative to external structure, such as the patient support structure, generally does not affect the position of the bracket 24 relative to the lumbosacral intervertebral disc space 16. Once the bracket 24 is in place on the iliac crest 20, a proximal end portion 27 of an iris retractor 28 may be attached to the pelvic bracket 24 so that a distal end 91 of the retractor 28 contacts or otherwise is brought into proximity with the laminae of the fifth lumbar vertebra L5 and the first sacral vertebra S1 at the site where the intervertebral lumbosacral disc space 16 will be manipulated.

Figure 2:
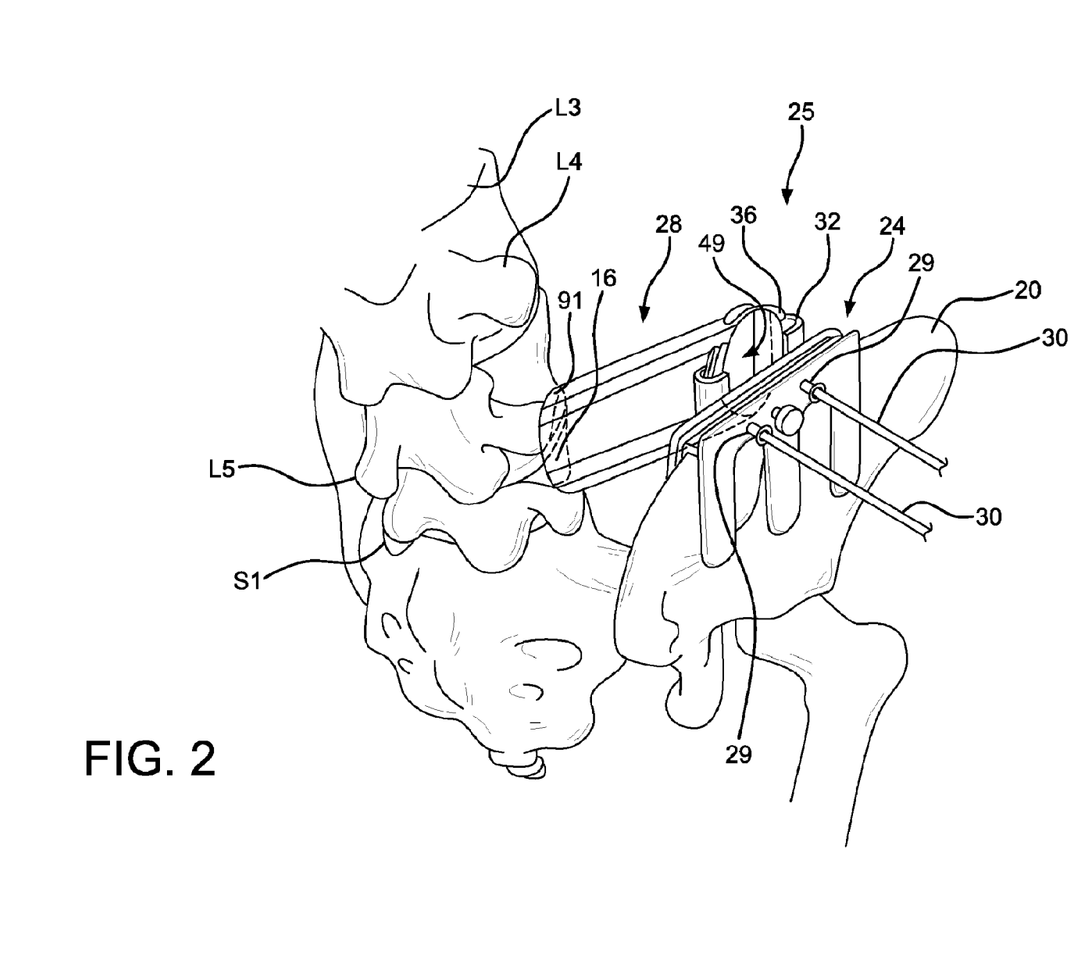
FIG. 2 is a side perspective view of a pelvic bracket and a retractor in accordance with a preferred embodiment of the present invention mounted to the lumbosacral region illustrated in FIG. 1.

For instance, the pelvic bracket 24 and the iris retractor 28 can include complementary engagement members that attach the pelvic bracket 24 to the retractor 28. In the preferred embodiment, the pelvic bracket 24 includes a pair of opposing bracket guides 32. The proximal end 27 of the iris retractor 28 can include one or more complementary engagement rails 36 that are configured to be slidably received within the bracket guides 32 to allow the iris retractor 28 to slide relative to the pelvic bracket 24. It should be appreciated that the bracket guides 32 can alternatively be disposed on the retractor 28 and the engagement rails 36 can be thus disposed on the pelvic bracket 24.

Figures 3A, 3B:
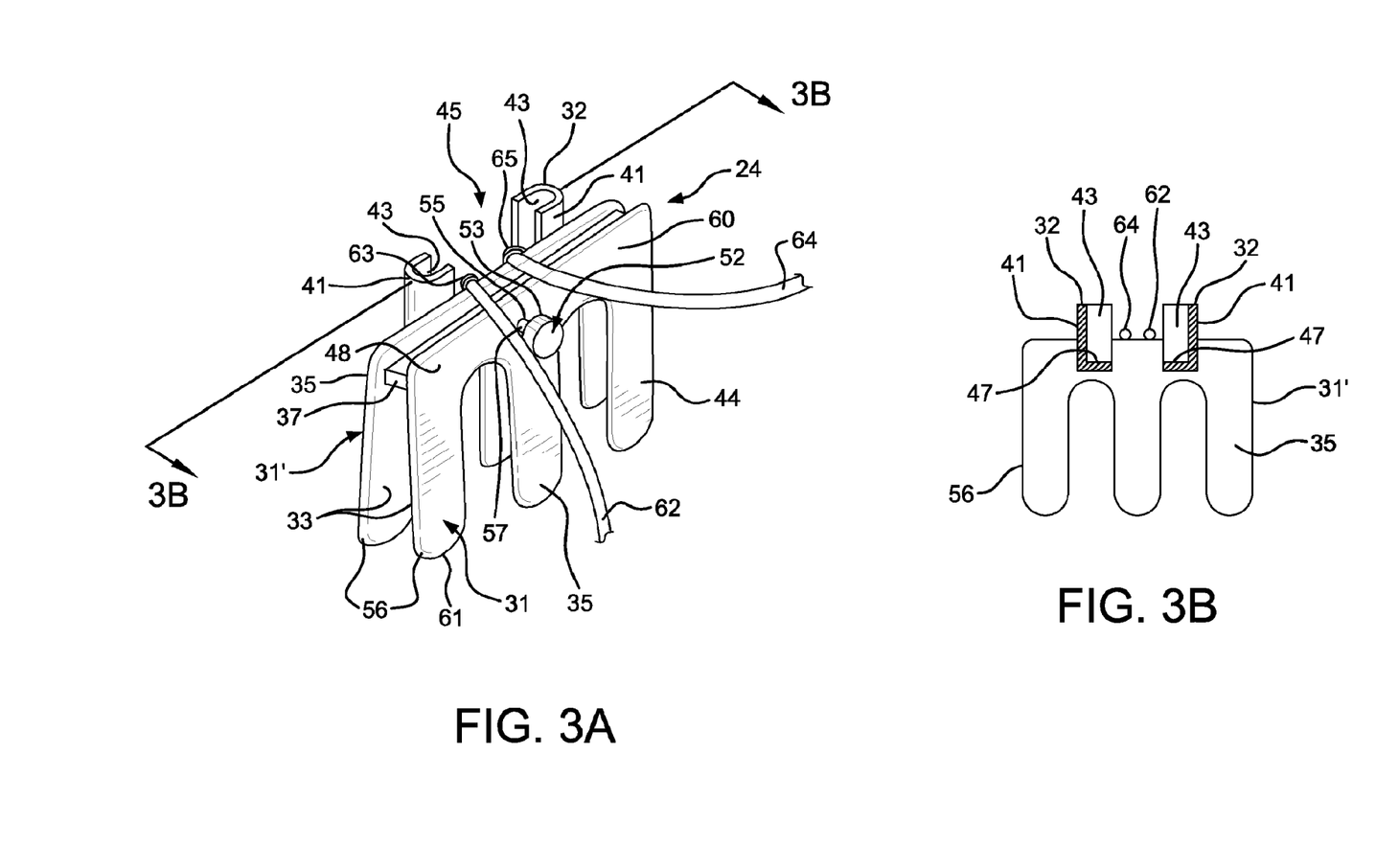
FIG. 3A is a side perspective view of the pelvic bracket illustrated in FIG. 2.
FIG. 3B is a cross-sectional view of the pelvic bracket illustrated in FIG. 3A, taken along line 3B-3B of FIG. 3A.

Referring to FIG. 3A, the pelvic bracket 24 is illustrated in a generally vertical orientation, though it should be appreciated that the orientation may be angularly offset from the vertical during use. The pelvic bracket 24 preferably includes a pair of laterally spaced plates 31 and 31', with a medial plate 31' being medially spaced from a lateral plate 31. The lateral and medial plates 31, 31' each preferably have a top portion 48 and a bottom portion 44. The lateral and medial plates 31, 31' are illustrated and described herein as being symmetrical, though the plates 31, 31' can be asymmetrically constructed if desired.

The lateral and medial plates 31, 31' of the preferred embodiment define inner surfaces 33 and opposing outer surfaces 35, and are positioned such that the inner surfaces 33 face each other in a mounted position. A spacer 37 is attached to the top portions 48 of the inner surfaces 33 of the lateral and medial plates 31, 31' so as to join the plates 31, 31' together.

The plates 31, 31' can be constructed of any suitable flexible, biocompatible material, such as a metal or plastic, such as stainless steel, and can flex laterally inwardly and outwardly about the spacer 37, thereby providing a clamp configured to receive the iliac crest 20, preferably at a posterior end.

One of the plates 31, 31', such as the lateral plate 31, can be provided with an adjustable locking fastener 52, illustrated as a thumbscrew 53, mounted onto the outer surface 35. The thumbscrew 53 preferably has a threaded shaft 55 that is threadedly received in a threaded aperture 57 extending laterally through the upper portion 48 of the plate 31 of the preferred embodiment. The shaft 55 has a distal end that is configured to engage the opposing medial plate 31' if, for instance, it is desired to tighten the plates 31, 31' together. While a thumbscrew 53 is illustrated as a representative example of the adjustable locking fastener 52, it should be appreciated that the fastener 52 is not intended to be limited to the thumbscrew 53 unless otherwise indicated, and any suitable fastener could alternatively be implemented.

Referring to FIG. 2, the lateral plate 31 can include one or more tether hooks 29 that can be fastened, for instance threadedly connected, to the top portions 48. A tether cable 30 can be attached to each hook 29 at a proximal end of the cable 30, and can be pulled taught so as to apply a force onto the pelvic bracket 24 that deflects the iliac crest 20 out of alignment with the lumbosacral intervertebral space 16 so as to allow enhanced visual access of the lumbosacral intervertebral disc space 16 during the surgical procedure. The distal ends of the tether cables 30 can be secured to any suitable structure capable of retaining the iliac crest 20 in its deflected position. The tether hooks 29 and cables 30 are shown removed from the bracket 24 in FIG. 3A for the purposes of clarity in illustrating the other components of the bracket 24.

Referring again to FIGS. 3A and 3B, the top portions 48 of each plate 31, 31' can include a horizontal beam 60 and the bottom portions 44 of each of the lateral and medial plates 31, 31' can include flexible fingers 56 configured to receive the iliac crest 20 therebetween. Each finger 56 preferably extends down from the horizontal beam 60 and defines a lower curved terminal end 61. Each finger 56 can be flexible so as to apply a retention force onto the iliac crest 20 to thereby secure the bracket 24 to the iliac crest 20. Each of the lateral and medial plates 31, 31' is illustrated as including three fingers 56, though it should be appreciated that the plates 31, 31' can include any number of fingers greater or equal to one, as deemed suitable to mount the bracket 24 onto the iliac crest 20. The lower portion 44 of each of the lateral and medial plates 31, 31' can additionally be curved anteriorly or posteriorly to approximate the shape of the iliac crest 20. It would be further appreciated that alternatively or additionally, the lower portion 44 of each of the lateral and medial plates 31, 31' can be a continuous plate portion as opposed to a plurality of fingers 56.

A pair of opposing bracket guides 32 is supported by the outer surface 35 of medial plate 31' in the preferred embodiment. Each bracket guide 32 includes a body 41 having a pair of spaced walls that, in combination, define a vertically elongate receptacle 43 which is U-shaped as illustrated, but is not geometrically limited to the size and shape illustrated. The receptacles 43 are sized and shaped to slidably receive the engagement rails 36 of the retractor 28. As shown in FIG. 3B, each bracket guide 32 can include a stop plate 47 extending across the lower end of each receptacle 43 so as to provide a seat for the engagement rails 36. Alternatively or additionally, the stop plate 47 can extend between the pair of bracket guides 32 so as to provide a seat for the engagement rails 36.

An opening of each receptacle 43 faces the opposing receptacle 43 so as to define a void 45 disposed between the bracket guides 32. One or more fiber optic lights 62 and/or cameras 64 may be attached to the bracket 24 to enhance visualization, and can define corresponding distal ends 63, 65 that are aligned with the void 45 so as to enable visualization through the retractor 28 once the retractor 28 is attached to the bracket 24. The camera 64 can provide visual input data to a display (not shown).

Referring now to FIGS. 4A-4D, the retractor 28 preferably includes a plurality of arc-shaped segments 68, each having a first portion 69 and a second portion 71 that telescopically receives the first portion 69. It should be appreciated, however, that each segment 68 can be rigid as opposed to telescopic. The first side 69 includes a longitudinally extending raised flange 72 at its circumferentially distal end, and the second side 71 includes a longitudinally extending expansion link 76 at its circumferentially distal end.

Figure 4A:
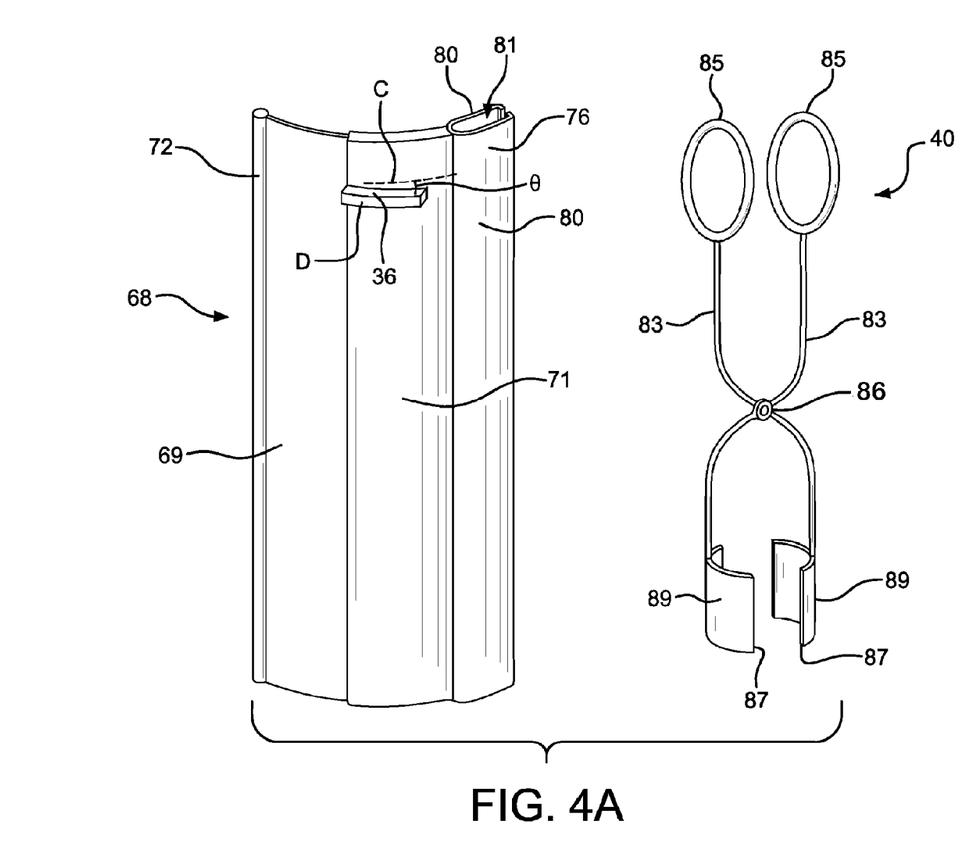
FIG. 4A is a top perspective view of a segment of the retractor illustrated in FIG. 2, and a preferred tool configured to expand the retractor.
Figure 4B:
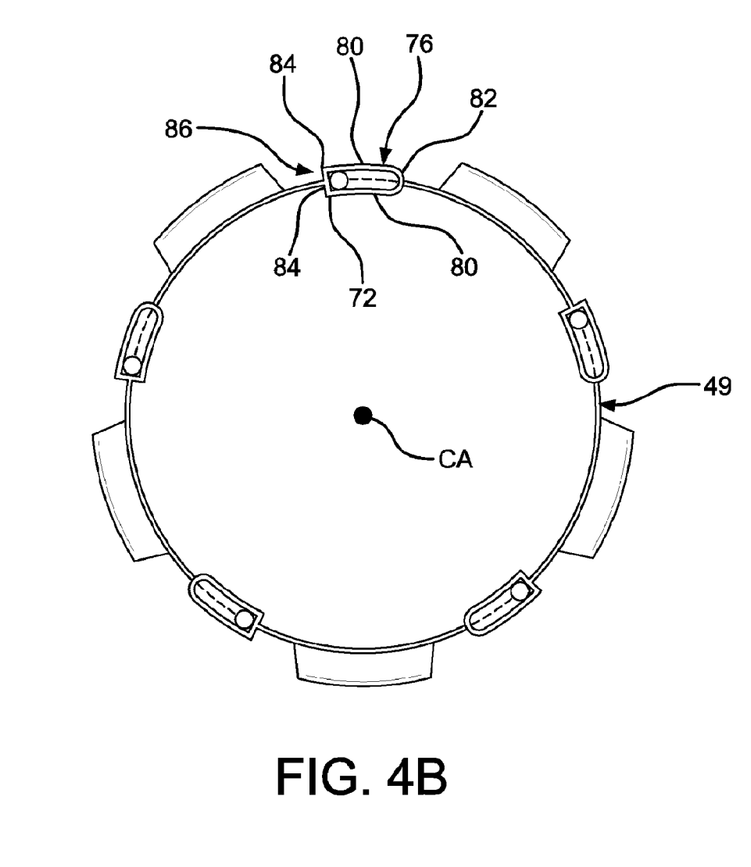
FIG. 4B is a top plan view of the retractor illustrated in FIG. 2, shown in an assembled configuration.
Figure 4C:
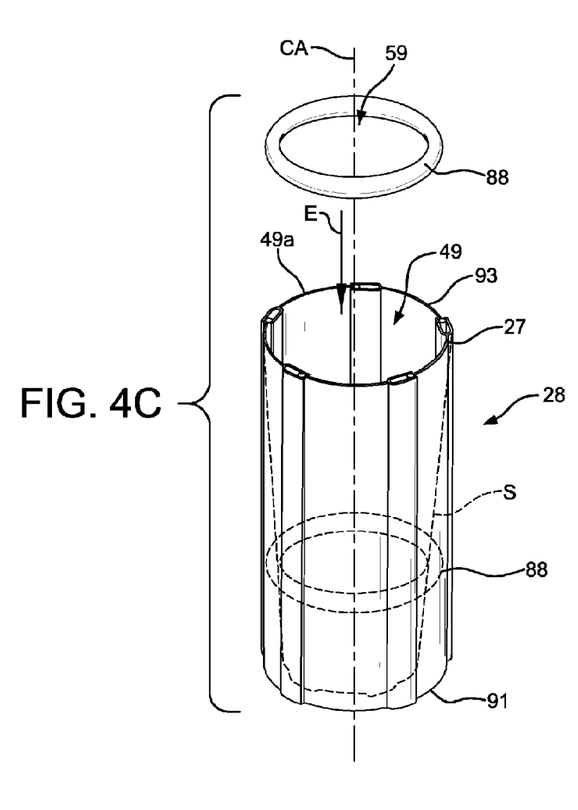
FIG. 4C is a top perspective view of the retractor illustrated in FIG. 4B.

Each expansion link 76 includes a pair of side walls 80 that extend from a generally rounded back wall 82. Side walls 80 are generally parallel to each other and include projections 84 that extend inward from the distal end of each side wall 80. The projections 84 define a dimension between each other that can be greater than or equal to zero, but less than the radius or outer dimension of the raised flange 72. Thus, the projections 84 are configured to interfere with the raised flange 72 so as to generally prevent separation of the adjoined expansion link 76.

Adjacent segments 68 can be connected by sliding the raised flange 72 of one segment 68 vertically into the channel 81 of the adjacent segment 68. Each expansion link 76 can include a stop plate 81a at the lower end of the channel 81 so as to define a seat for the raised flange 72 of the adjacent segment 68. Upon assembly of a plurality of segments 68, a complete cylinder may be formed that extends about a central axis CA that extends centrally between the proximal end distal ends of the retractor 28. The formation of a complete cylinder is preferable, so as to prevent surrounding organs and tissue from readily infiltrating or creeping into the surgical field during the surgical procedure. The cylindrical retractor 28 defines a cylindrical channel 49 configured to receive surgical instruments 90 in the mounted position. As shown in FIG. 2, the channel 49 may partially overlap or project into the iliac crest 20 and bracket 24.

The retractor 28 preferably defines a distal end 91 configured to be positioned over the lumbosacral intervertebral disc space 16 and an opposing proximal end 93 configured to attach to the pelvic bracket 24. As illustrated, an outer edge 95 is preferably disposed at the proximal end 93 and defines a cylindrical opening 49a into the channel 49 (see FIG. 4B) that is configured to receive a surgical tool 90 (see FIG. 5).

Figure 4D:
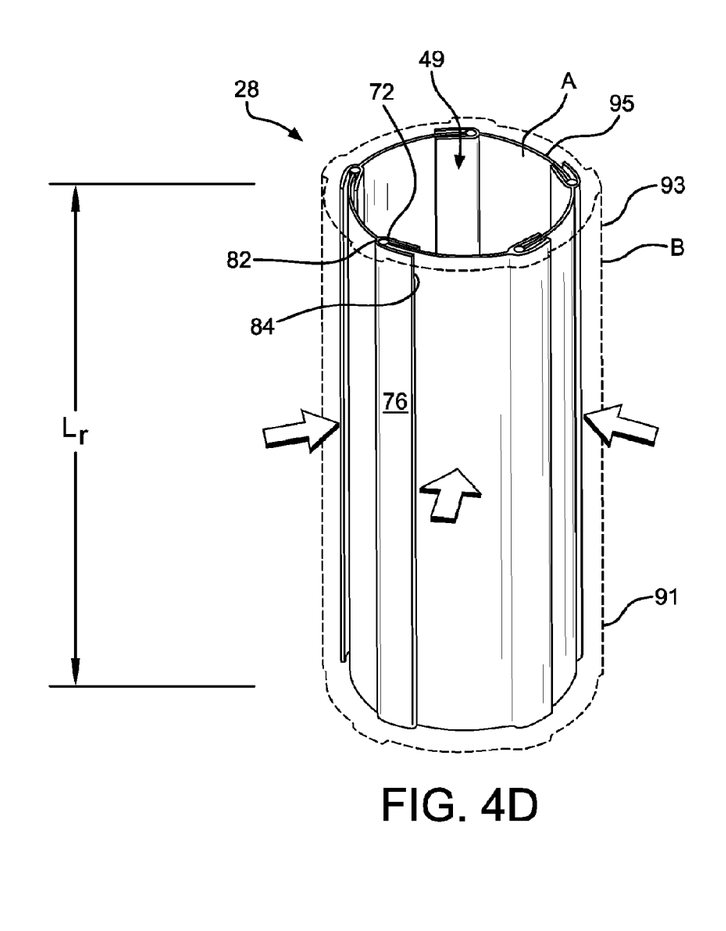
FIG. 4D is a top perspective view of portions of the retractor illustrated in FIG. 4B, showing the retractor both in a retracted position and in a distracted position in phantom linetype.

The cooperation of the expansion link 76 and the raised flange 72 of the adjacent expansion links 76 permits adjustment between a retracted position and a distracted position. For example, as shown in FIG. 4D, when the retractor 28 is in a fully retracted position A, each raised flange 72 abuts a back wall 82 of a respective expansion link 76. Conversely, when retractor 28 is in a fully distracted position B (shown in phantom linetype), each flange 72 abuts the inner surfaces of projections 84 of a respective expansion link 76. In this regard, it should be appreciated that in the retracted position A, the flange 72 is disposed closer to the back wall 82 than when in the distracted position B and in the distracted position B, the flange 72 is disposed closer to the projections 84 than when in the retracted position A. Accordingly, the retractor 28 can iterate between a smaller inner dimension (inner diameter as illustrated) in its retracted position A and a larger inner dimension (inner diameter as illustrated) in its distracted position B.

An expansion tool 40 is preferably provided that is configured to adjust the position of the retractor 28. In the preferred embodiment, the expansion tool 40 includes a pair of reciprocating arms 83 pivotally connected to each other at a joint 86. The arms 83 are each connected to a handle 85 at a proximal end and to a biasing member 87 at a distal end. The biasing members 87 can include arc-shaped outer surfaces 89 having a curvature that corresponds generally to inner surfaces of the arc-shaped segments 68 of the retractor 28. Accordingly, biasing members 87 can be inserted into the retractor 28 and the handles 85 can be separated, thereby causing the outer surfaces 89 to impart a radially outward biasing force onto the segments 68, thereby urging the retractor 28 to translate from the refracted position A to the distracted position B.

It should be appreciated that the expansion tool 40 is merely illustrative of one example of a suitable apparatus configured to expand the retractor 28 and is not intended to be limiting. It is contemplated to use any manual or motorized system suitable for retraction and distraction of the retractor 28. In addition, referring to FIG. 4C, if the surgeon desires to produce a more frusto-conical shape, so as to create a broader window at the distal end 91 of the retractor 28 over the lumbosacral intervertebral disc space 16, an annular insert 88 may define an opening 59 sized slightly less than the outer diameter of the retractor 28 when in the distracted position B, but greater than the outer diameter of the retractor 28 when in the retracted position A. Accordingly, when the retractor 28 is in the distracted position B, the insert 88 can receive the retractor 28 and be translated along the retractor 28 in the direction of Arrow E to a depth of choice with respect to the proximal end 93. The insert 88 can be constructed of any suitable material, such as medical-grade stainless steel. The resulting compression at the proximal end 93 will enable creation of a frusto-conical shape S (shown in dashed linetype in FIG. 4C) that results from the distal end 93 being distracted greater than the proximal end 91. Since patient anatomies are such that depths of at least about one hundred twenty to one hundred eighty millimeters (120-180 mm) may be desired, preferably depth of approximately one hundred ten to one hundred fifty millimeters (110-150 mm), it is further contemplated that each of the segments 68 be capable of longitudinal expansion, for example by forming in two parts with a telescoping ability, so as to accommodate differing patient anatomies.

Figure 4E:
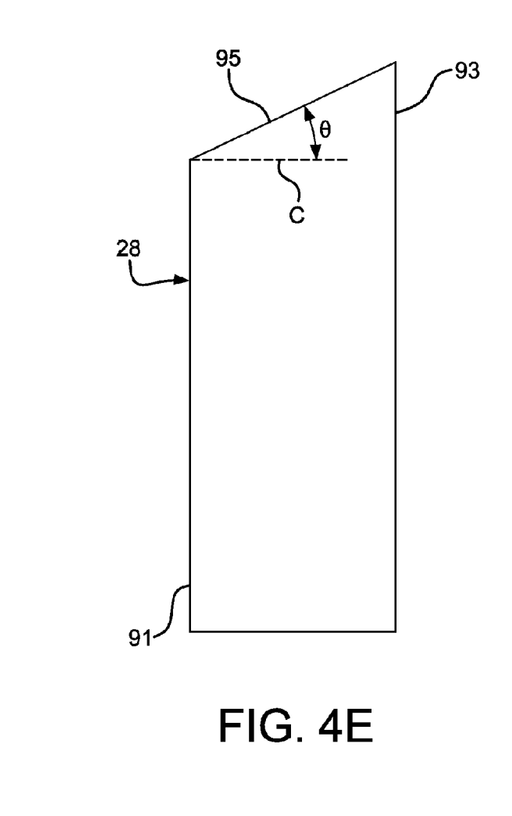
FIG. 4E is a schematic side elevation representative view of the retractor illustrated in FIG. 4D.

Referring to FIGS. 4A and 4E, each segment 68 preferably includes an engagement rail 36 that extends in a direction D that is angularly offset with respect to a plane C that extends generally perpendicular to the central axis CA. In particular, the engagement rails 36 that are inserted into the bracket guides 32 define an angle θ with respect to the plane C that extends perpendicular to the central axis CA. The outer edge 95 is preferably oriented in a direction at an angle θ with respect to the plane C. Thus, when the retractor 28 is attached to the bracket 24 such that the outer edge 95 extends parallel to the medial plate 31', the retractor segments 68 extend from the bracket 24 at the angle θ with respect to the medial plate 31', thereby directing the distal end 91 to the lumbosacral intervertebral disc space 16, as illustrated in FIG. 2. The angle θ can be anywhere between about fifteen degrees)(15°) and about sixty degrees)(60°) with respect to the plane C, and in certain preferred embodiments can be anywhere between about twenty degrees and twenty-five degrees (20° and 25°). Thus, it should be appreciated that the retractor 28 (or central axis CA) can extend at a desired downward angle between about twenty and fifty degrees (20°-50°) with respect to the anteroposterior direction in certain preferred embodiments, or define an angle between about forty and seventy degrees (40°-70°) with respect to the caudocranial direction. Alternatively still, the retractor 28 (or central axis CA) can extend at a downward angle between about twenty-five and forty degrees (25°-40°) with respect to the anteroposterior direction, or between about fifty and sixty-five degrees (50°-65°) with respect to the caudocranial direction Each engagement rail 36 preferably has a size and shape suitable to be inserted into one of the bracket guides 32 in the manner described above. Inserting the engagement rails 36 into the bracket guides 32 generally fixes the retractor 28 at a fixed angle relative to the medial plate 31' in a position suitable to position the distal end 91 over the lumbosacral intervertebral disc space 16 while the proximal end 93 provides a sufficient entry space for the surgeon to insert one or more surgical tools 90 (shown in FIG. 5) to facilitate a surgical procedure on the lumbosacral area of the spine. While each segment 68 includes an engagement rail 36, it should be appreciated in the illustrated embodiment that only a pair of opposing rails 36 can be inserted into the bracket guides 32 in order to attach the retractor 28 to the bracket 24, as illustrated in FIG. 2. In this regard, the retractor 28 includes only a pair of opposing, or circumferentially spaced, engagement rails 36 in an alternative embodiment.

It is understood that nerve guidance and fluoroscopy can be utilized throughout the procedure in order to avoid nerves and vessels during the lateral transpsoas approach.

Figure 5:
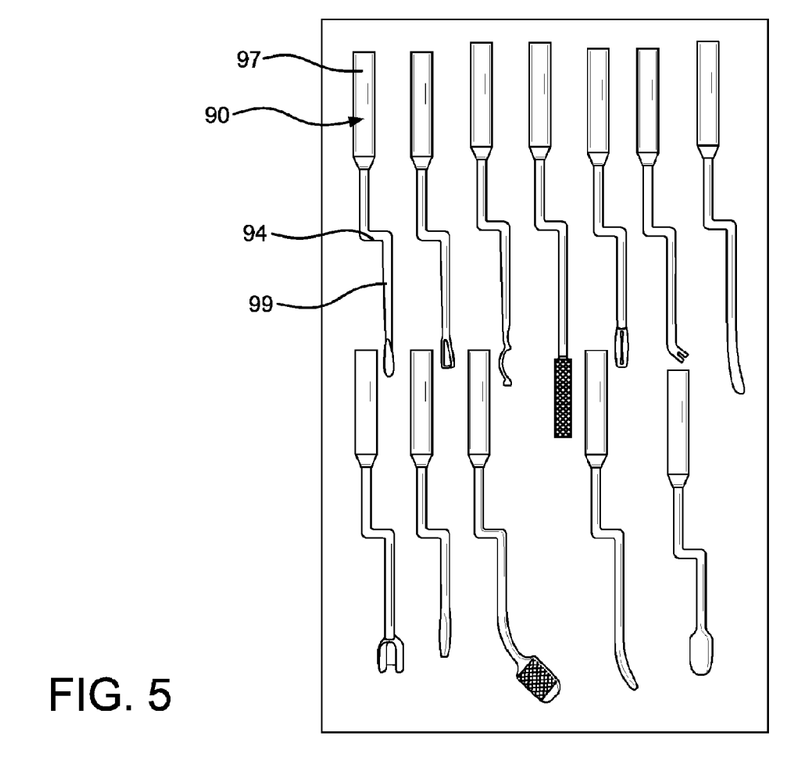
FIG. 5 is a top plan view showing several components of an offset tool kit configured to insert a trial implant into an intervertebral disc space in accordance with the preferred embodiment of the present invention.

As further illustrated in FIG. 5, a kit of offset tools 90 is provided for enabling the performance of annulotomy and intervertebral disc space preparation. The tool 90 can be provided, for instance, as pituitary rangeurs, curettes, disc cutters, scrapers and the like. Each tool 90 preferably includes a handle end 97 and an opposing working end 99 joined by an offset portion 94. The offset portion 94 allows the surgeon to grip the handle end 97 while directing the working end 99 to the lumbosacral intervertebral disc space 16 through the access point provided by retractor 28. Components of the kit may include, but are not limited to, one or more of chisels, disc cutters, rasps, pituitary rongeurs, scrapers, curettes, cobb elevators, sizers, broaches or the like tools known to be useful for such procedures.

Figure 6A:
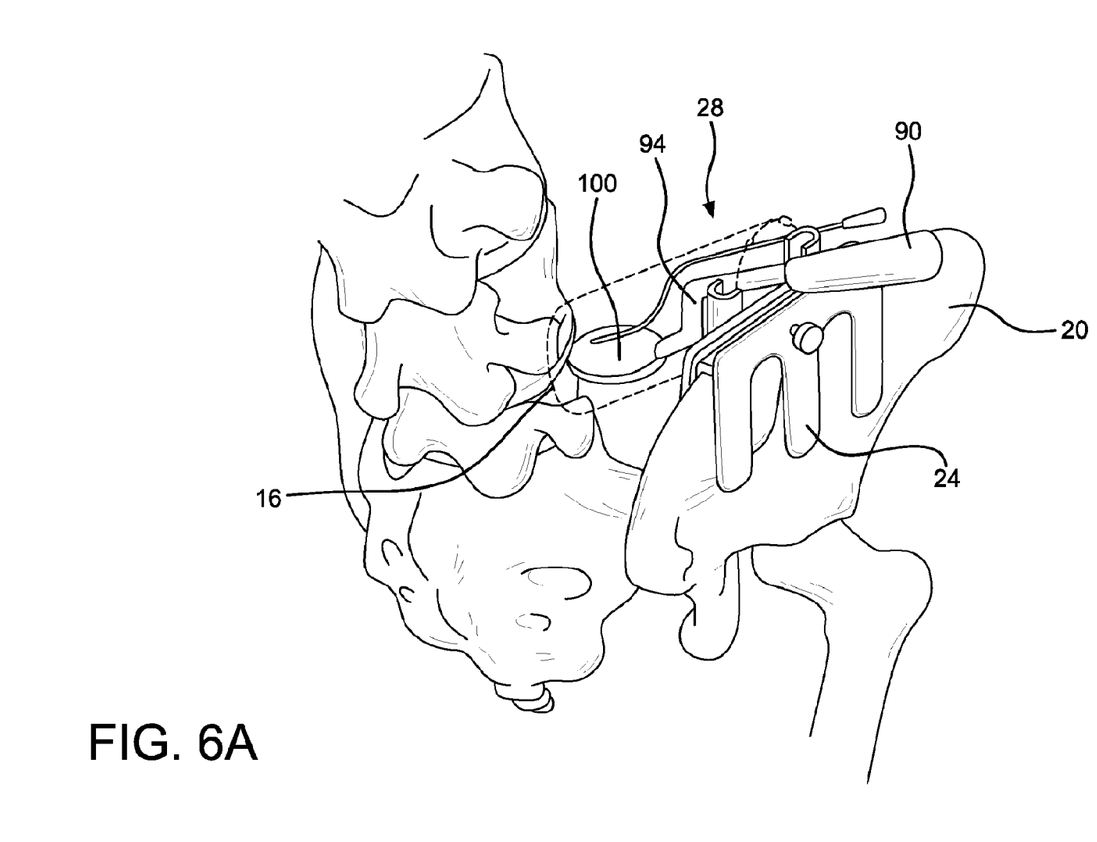
FIG. 6A is a side perspective view of the pelvic bracket and the retractor illustrated in FIG. 2 mounted in the lumbosacral region of the human torso as illustrated in FIG. 2 and also showing an oval-shaped trial implant being laterally inserted through the retractor.

Referring now to FIG. 6A, an intervertebral insert such as a trial implant 100 is connected to the working end 99 of the tool 90. Depending on the type of procedure and patient's anatomical structure, oval and tapered trial implants 100 may be provided and selected for ease of insertion within the lumbosacral intervertebral disc space 16. The implants that may be inserted into the prepared disc space 16 are generally filled with graft material (not shown), such as bone morphogenic protein. The tool 90 may be used to establish a desired placement of the implant. As shown, the offset portion 94 of tool 90 further aids the surgeon's ability to maneuver around iliac crest 20.

Figure 6B:
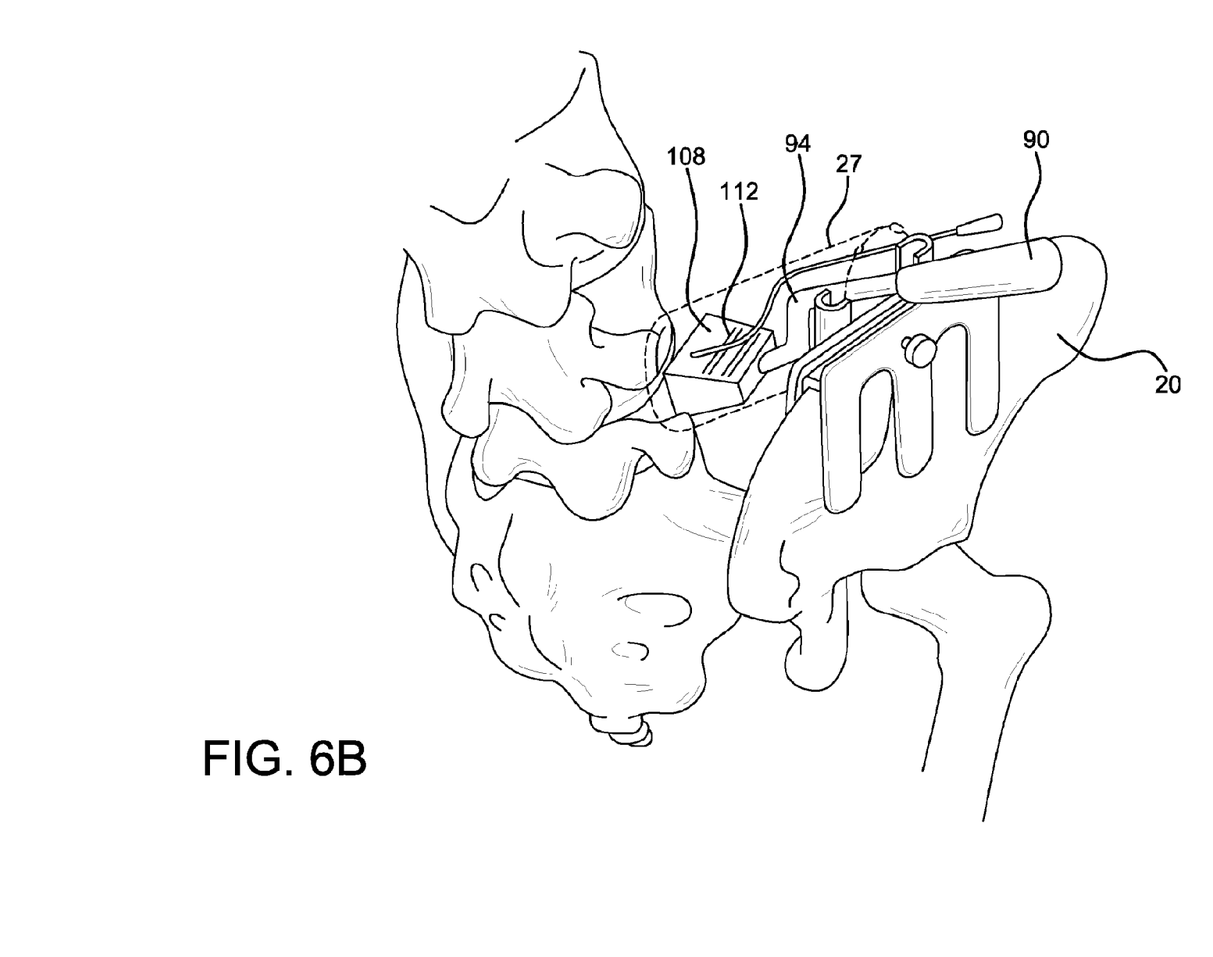
FIG. 6B is a side perspective view of the pelvic bracket and the retractor illustrated in FIG. 2 mounted in the lumbosacral region of the human torso as illustrated in FIG. 2 and also showing a wedge-shaped implant being laterally inserted through the retractor.

Referring to FIG. 6B, an alternative implant design is shown wherein a condition such as scoliosis may be treated. This involves using a wedge-shaped implant 108, which may include anti-skid treads 112. The implant 108 may be provided in various angulations, e.g. between about fifteen to sixty degrees (15°-60°) with respect to the anteroposterior direction, in increments of about fifteen degrees)(15°. The implant 108 may be designed to cooperate with the tool 90, which in the preferred embodiment is an offset shim inserter that is capable of slidably and threadably engaging the implant 108 for ease of insertion and ultimate release. Such shim-like implants 108 will enable correction of the positioning of asymmetrically shaped vertebrae or the like.

It should be appreciated thus that the surgical kit 25 can provide methods for providing lateral access to an intervertebral disc space when performing surgical procedures. For example, a surgical procedure can be initiated with the patient laterally positioned on a radiolucent surgical table. Fluoroscopy in the anterior-posterior and lateral views is used to locate the affected intervertebral disc space. The surgeon utilizes anatomic landmarks, such as the iliac crest, twelfth ($12^{th}$) rib, the lateral border of the erector spinae muscles, or the like, in order to calculate placement of the initial incision. Guide wires (not shown) may or may not be used during the procedure. The incision exposes the iliac crest 20, and the surgeon mounts the pelvic bracket 24 onto the iliac crest 20, in the manner described herein, once the incision has been made.

The tissue can be dilated and the iris retractor 28 can subsequently be attached to the pelvic bracket 24 in the manner described above. For instance, the iris retractor 28 can be in its retracted configuration and the engagement rails 36 will be slidably positioned within the bracket guides 32. Subsequently the retractor 28 may be distracted, for example, using the expansion tool 40 illustrated in FIG. 4, as described above.

Various methods of tissue dilation may be carried out as are known in the art. For example, a single guide wire may be utilized and a sequence of sequential dilators is positioned over the single guide wire. Sequentially larger dilators are preferably positioned one over the other to receive a circular retractor of desired size. Alternatively, a series of blade dilators, modified to have a flared distal end in accordance with certain aspects of the present invention, is utilized to establish an operative corridor at the lumbosacral intervertebral disc space 16.

The procedure is preferably continued using modified distracters and sizers, which enable distraction of the intervertebral disc space 16 and testing of trial implants 100. AP fluoroscopy is preferably utilized when impacting the trial 100 in place and lateral fluoroscopy is then preferably used in order to verify proper anterior/posterior position. The trial implant 100 or any suitable alternative trial implant can be attached to a tool, such as the tool 90 illustrated in FIG. 5, and the trial implant 100 can be inserted into the lumbosacral intervertebral disc space 16. Dependent upon the type of procedure and patient's anatomical structure, oval and tapered trail implants 100 may be provided and selected for ease of insertion within the lumbosacral intervertebral disc space 16. AP fluoroscopy and EMG can be utilized during positioning of the trial implant 100.

It is to be understood that while certain embodiments are illustrated, the invention is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art, which are encompassed within the spirit of the invention and are defined by the scope of the appended claims. Although the invention has been described in connection with a specific preferred embodiment, it should be understood that the invention as claimed should not be unduly limited to such specific embodiments. Indeed, various modifications of the described modes for carrying out the invention which are obvious to those skilled in the art are intended to be within the scope of the following claims.

I claim:

1. A surgical kit for laterally accessing a lumbosacral intervertebral disc space by engaging an iliac crest of a patient, the kit comprising:
    a bracket including a pair of laterally spaced plates, each of the pair of laterally spaced plates defining an inner surface that faces the inner surface of the other of the pair of laterally spaced plates, the pair of laterally spaced plates defining a receiving space between the inner surfaces, the receiving space sized and configured to receive the iliac crest so as to mount the bracket onto the iliac crest, and each of the pair of laterally spaced plates including a top portion and a bottom portion, wherein the top portions of each of the pair of laterally spaced plates are connected such that the receiving space between the inner surfaces of the top portions is fixed, and the bottom portions are movable relative to one another such that the receiving space between the inner surfaces of the bottom portions is adjustable;
    a refractor defining a channel that is elongate in a longitudinal direction, the retractor including a proximal end defining a first opening that is open to the channel, the retractor further including a distal end opposite the proximal end, the distal end defining a second opening that is open to the channel, such that when the retractor is attached to the bracket and the bracket is mounted to the iliac crest, 1) the channel extends toward and is aligned with the lumbrosacral intervertebral disc space along the longitudinal direction such that the second opening faces the lumbosacral disc space, 2) at least one of the pair of laterally spaced plates overlaps at least a portion of the first opening along the longitudinal direction, and 3) the at a least a portion of the first opening is positioned between the at least one of the pair of laterally spaced plates and the second opening with respect to the longitudinal direction;
    wherein the retractor defines an inner dimension measured across the channel in a direction perpendicular to the longitudinal direction, and the retractor is movable between a retracted position and a distracted position, whereby the inner dimension is larger when the retractor is in the distracted position than when the retractor is in the retracted position.

2. The kit of claim 1, wherein the retractor includes a plurality of segments, each of the plurality of segments has a first portion having a longitudinally extending raised flange and a second portion having a longitudinally extending expansion link, and the flange of each of the plurality of segments is received in the expansion link of an adjacent segment of the plurality of segments.

3. The kit of claim 2, wherein each of the plurality of segments is connected to the adjacent segment of the plurality of segments to create a cylindrical tube.

4. The kit of claim 1, wherein the bracket includes engagement rails and the retractor includes guides that are slidably engageable with the engagement rails.

5. The kit of claim 1, wherein the bracket includes bracket guides and the retractor includes engagement rails that are configured to be slidably received within the bracket guides.

6. The kit of claim 5, wherein each of the bracket guides comprises a body having a pair of spaced walls.

7. The kit of claim 6, wherein the pair of spaced walls define a vertically elongate U-shaped receptacle.

8. The kit of claim 5, wherein the bracket guides include a stop plate extending across a lower end of each of the bracket guides.

9. The kit of claim 1, wherein at least one of the pair of laterally spaced plates comprises flexible fingers.

10. The kit of claim 1, wherein the retractor comprises an interior, the interior of the retractor being accessible after the retractor has been directly attached to the bracket.

11. The kit of claim 1, wherein one of the pair of laterally spaced plates includes an adjustable locking fastener.

12. The kit of claim 11, wherein the adjustable locking fastener is a thumbscrew.

13. The kit of claim 12, wherein the adjustable locking fastener engages each of the pair of laterally spaced plates, such that when the adjustable locking fastener is tightened the pair of laterally spaced plates are drawn together.

14. The kit of claim 1, wherein the bracket includes at least one tether hook that when pulled taut applies a force to the bracket and deflects the iliac crest.

15. The kit of claim 1, wherein the retractor includes a plurality of arc shaped elements, each of the plurality of arc shaped elements having a first portion and a second portion that telescopically receives the first portion.

16. The kit of claim 1, further comprising one or more fiber optic lights or cameras that are attached to the bracket.

17. The kit of claim 1, wherein the retractor is attachable directly to the bracket such that the retractor is positioned entirely outside of the receiving space.

18. The kit of claim 1, wherein the retractor is attachable directly to the top portion of a first of the pair of laterally spaced plates of the bracket.

19. The kit of claim 1, wherein the retractor defines a retractor length measured from the first opening to the second opening in the longitudinal direction, the kit further comprising at least one tool having an elongated handle and a shaft, the shaft having a shaft length, the shaft length being greater than the retractor length.

20. The kit of claim 1, further comprising
an annular insert that defines an outer diameter that is smaller than the inner dimension when the retractor is in the distracted position and larger than the inner dimension when the retractor is in the retracted position, wherein the annular insert is configured to be inserted into the channel and advanced in the longitudinal direction to gradually increase the inner dimension of the retractor.

21. The kit of claim 1, wherein the pair of laterally spaced plates are spaced apart from each other in a lateral direction to define the receiving space, and the at least one of the pair of laterally spaced plates faces the first opening in the lateral direction.

22. A surgical kit for laterally accessing a lumbosacral intervertebral disc space by engaging an iliac crest of a patient, the kit comprising:
a bracket including a pair of laterally spaced plates, each of the pair of laterally spaced plates defining an inner surface that faces the inner surface of the other of the pair of laterally spaced plates, the pair of laterally spaced plates defining a receiving space between the inner surfaces, the receiving space sized and configured to receive the iliac crest so as to mount the bracket onto the iliac crest, and each of the pair of laterally spaced plates including a top portion and a bottom portion, the bracket further including at least one tether hook that when pulled taut applies a force to the bracket and deflects the iliac crest, wherein the top portions of each of the pair of laterally spaced plates are connected such that the receiving space between the inner surfaces of the top portions is fixed, and the bottom portions are movable relative to one another such that the receiving space between the inner surfaces of the bottom portions is adjustable;
a refractor that defines a channel that is elongate in a longitudinal direction, the refractor including a proximal end that defines a first opening that is open to the channel, the retractor further including a distal end opposite the proximal end that defines a second opening that is open to the channel, such that when the retractor is attached to the bracket and the bracket is mounted to the iliac crest, 1) the channel is configured to extend toward and align with the lumbrosacral intervertebral disc space along the longitudinal direction, and 2) at least one of the pair of laterally spaced plates at least partially overlaps the first opening along the longitudinal direction;
wherein the retractor defines an inner dimension measured across the channel in a direction perpendicular to the longitudinal direction, and the retractor is movable between a retracted position and a distracted position, whereby the inner dimension is larger when the retractor is in the distracted position than when the retractor is in the retracted position.

23. The kit of claim 22, wherein the retractor includes a plurality of segments, each of the plurality of segments has a first portion that includes a longitudinally extending raised flange and a second portion that includes a longitudinally extending expansion link, and the flange of each of the plurality of segments is configured to be received in the expansion link of an adjacent segment of the plurality of segments.

24. The kit of claim 23, wherein each of the plurality of segments is substantially arc shaped, and the second portion of each of the plurality of segments is configured to telescopically receive the first portion of the respective one of the plurality of segments.

25. The kit of claim 22, wherein at least one of the pair of laterally spaced plates comprises flexible fingers.

26. A surgical kit for laterally accessing a lumbosacral intervertebral disc space by engaging an iliac crest of a patient, the kit comprising:
a bracket configured to be mounted to the iliac crest; and
a refractor that is attachable to the bracket and elongate in a longitudinal direction, the retractor including a plurality of segments, each of the plurality of segments having a first portion having a longitudinally extending raised flange and a second portion having a longitudinally extending expansion link that is configured to receive the raised flange of an adjacent one of the plurality of segments, each of the plurality of segments defining a respective length measured from the respective longitudinally extending raised flange to the respective longitudinally extending expansion link, each expansion link including a back wall and a pair of side walls that are spaced from each other so as to define a channel that receives the raised flange of the adjacent one of the plurality of segments, and each of the pair of side walls including a projection that extends toward the projection of the other of the pair of side walls, the projections of each of the pair of side walls of each of the plurality of segments being configured to interfere with the received raised flange so as to prevent removal of the received raised flange from the channel, wherein the first portion of a first of the plurality of segments is movable relative to and at least partially receivable within the second portion of the first of the plurality of segments such that the length of the first of the plurality of segments is adjustable, such that the retractor is movable between a retracted position and a distracted position, whereby the length is larger when the retractor is in the distracted position than when the retractor is in the retracted position.

27. The kit of claim 26, wherein the retractor defines a retractor length measured along the longitudinal direction, and the kit further comprises at least one tool having an elongated handle and a shaft, the shaft having a shaft length, the shaft length being greater than the retractor length.

28. The kit of claim 26, wherein the bracket includes a pair of laterally spaced plates, each of the pair of laterally spaced plates defining an inner surface that faces the inner surface of the other of the pair of laterally spaced plates, the pair of laterally spaced plates defining a receiving space between the inner surfaces, the receiving space configured to receive the iliac crest so as to mount the bracket onto the iliac crest.

29. The kit of claim 26, wherein the bracket includes at least one tether hook that when pulled taut applies a force to the bracket and deflects the iliac crest.

30. The kit of claim 26, wherein when the raised flange of each of the plurality of segments is received within the expansion link of the adjacent one of the plurality of segments the raised flange of each of the plurality of segments moves toward the projections and away from the back wall of the adjacent one of the plurality of segments when the retractor is moved from the retracted position to the distracted position.

31. The kit of claim 26, wherein the pair of side walls are generally parallel to each other.

\* \* \* \* \*

UNITED STATES PATENT AND TRADEMARK OFFICE
CERTIFICATE OF CORRECTION

PATENT NO.         : 8,808,172 B2                                      Page 1 of 1
APPLICATION NO.    : 12/991018
DATED              : August 19, 2014
INVENTOR(S)        : James Manzanares It is certified that error appears in the above-identified patent and that said Letters Patent is hereby corrected as shown below:

IN THE CLAIMS

Claim 22, column 12, line 9, delete "refractor" and insert --retractor--.

Signed and Sealed this
First Day of March, 2016

Michelle K. Lee
*Director of the United States Patent and Trademark Office*